United States Patent
Helliwell et al.

(10) Patent No.: US 11,351,124 B2
(45) Date of Patent: Jun. 7, 2022

(54) SUSTAINED RELEASE OF FORMULATIONS OF LOCAL ANESTHETICS

(71) Applicant: EUPRAXIA PHARMACEUTICALS INC., Victoria (CA)

(72) Inventors: James A. Helliwell, Victoria (CA); Amanda Malone, Victoria (CA); Rafi Chapanian, Victoria (CA); Richard Liggins, Victoria (CA)

(73) Assignee: Eupraxia Pharmaceuticals Inc., Victoria (CA)

( * ) Notice: Subject to any disclaimer, the term of this patent is extended or adjusted under 35 U.S.C. 154(b) by 113 days.

(21) Appl. No.: 15/770,414

(22) PCT Filed: Oct. 27, 2016

(86) PCT No.: PCT/US2016/059141
§ 371 (c)(1),
(2) Date: Apr. 23, 2018

(87) PCT Pub. No.: WO2017/075232
PCT Pub. Date: May 4, 2017

(65) Prior Publication Data
US 2018/0311173 A1 Nov. 1, 2018

Related U.S. Application Data

(60) Provisional application No. 62/247,159, filed on Oct. 27, 2015.

(51) Int. Cl.
*A61K 9/50* (2006.01)
*A61K 9/00* (2006.01)
(Continued)

(52) U.S. Cl.
CPC .......... *A61K 9/5026* (2013.01); *A61K 9/0024* (2013.01); *A61K 9/0085* (2013.01);
(Continued)

(58) Field of Classification Search
None
See application file for complete search history.

(56) References Cited

U.S. PATENT DOCUMENTS

| 2,515,898 A | 7/1950 | Rhodehamel, Jr. |
| 2,627,491 A | 2/1953 | Szabo et al. |

(Continued)

FOREIGN PATENT DOCUMENTS

| CN | 1679515 A | 10/2005 |
| CN | 102070895 A | 5/2011 |

(Continued)

OTHER PUBLICATIONS

International Search Report and Written Opinion; dated Jan. 19, 2017, for International Application No. PCT/US2016/059141; 11 pages.

(Continued)

*Primary Examiner* — Bethany P Barham
*Assistant Examiner* — Barbara S Frazier
(74) *Attorney, Agent, or Firm* — Seed IP Law Group LLP

(57) ABSTRACT

Described herein are sustained release formulations of polymer-coated local anesthetic agents, and methods for using the same to relieve or manage pain, including postsurgical pain.

17 Claims, 8 Drawing Sheets

(51) Int. Cl.
*A61K 31/445* (2006.01)
*A61P 23/02* (2006.01)
(52) U.S. Cl.
CPC .......... *A61K 9/5089* (2013.01); *A61K 31/445* (2013.01); *A61P 23/02* (2018.01)

(56) References Cited

U.S. PATENT DOCUMENTS

| | | | |
|---|---|---|---|
| 3,867,519 A | 2/1975 | Michaels | |
| 3,993,073 A | 11/1976 | Zaffaroni | |
| 4,105,776 A | 8/1978 | Ondetti et al. | |
| 4,231,938 A | 11/1980 | Monaghan et al. | |
| 4,244,836 A * | 1/1981 | Frensch | A01N 25/28 |
| | | | 264/4.6 |
| 4,316,906 A | 2/1982 | Ondetti et al. | |
| 4,337,201 A | 6/1982 | Petrillo, Jr. | |
| 4,344,949 A | 8/1982 | Hoefle et al. | |
| 4,346,227 A | 8/1982 | Terahara et al. | |
| 4,374,829 A | 2/1983 | Harris et al. | |
| 4,410,520 A | 10/1983 | Watthey | |
| 4,427,649 A | 1/1984 | Dingle et al. | |
| 4,439,196 A | 3/1984 | Higuchi | |
| 4,444,784 A | 4/1984 | Hoffman et al. | |
| 4,508,729 A | 4/1985 | Vincent et al. | |
| 4,512,924 A | 4/1985 | Attwood et al. | |
| 4,530,840 A | 7/1985 | Tice et al. | |
| 4,542,025 A | 9/1985 | Tice et al. | |
| 4,568,559 A | 2/1986 | Nuwayser et al. | |
| 4,587,258 A | 5/1986 | Gold et al. | |
| 4,623,588 A | 11/1986 | Nuwayser et al. | |
| 4,652,441 A | 3/1987 | Okada et al. | |
| 4,675,196 A | 6/1987 | Villa et al. | |
| 4,739,073 A | 4/1988 | Kathawala | |
| 4,757,128 A | 7/1988 | Domb et al. | |
| 4,789,724 A | 12/1988 | Domb et al. | |
| 4,857,311 A | 8/1989 | Domb et al. | |
| 4,888,176 A | 12/1989 | Langer et al. | |
| 4,897,402 A | 1/1990 | Duggan et al. | |
| 4,904,646 A | 2/1990 | Karanewsky et al. | |
| 4,906,624 A | 3/1990 | Chucholowski et al. | |
| 4,906,657 A | 3/1990 | Roth | |
| 4,920,109 A | 4/1990 | Onishi et al. | |
| 4,923,861 A | 5/1990 | Picard et al. | |
| 4,929,620 A | 5/1990 | Chucholowski et al. | |
| 4,939,143 A | 7/1990 | Regan et al. | |
| 4,940,727 A | 7/1990 | Inamine et al. | |
| 4,940,800 A | 7/1990 | Bertolini et al. | |
| 4,946,860 A | 8/1990 | Morris et al. | |
| 4,946,864 A | 8/1990 | Prugh et al. | |
| 4,950,675 A | 8/1990 | Chucholowski | |
| 4,957,940 A | 9/1990 | Roth | |
| 4,963,538 A | 10/1990 | Duggan et al. | |
| 4,968,693 A | 11/1990 | Joshua et al. | |
| 4,970,231 A | 11/1990 | Lee et al. | |
| 4,992,429 A | 2/1991 | Ullrich et al. | |
| 4,994,281 A | 2/1991 | Muranishi et al. | |
| 4,994,494 A | 2/1991 | Regan et al. | |
| 4,996,234 A | 2/1991 | Regan et al. | |
| 4,997,837 A | 3/1991 | Chucholowski et al. | |
| 5,001,128 A | 3/1991 | Neuenschwander et al. | |
| 5,001,144 A | 3/1991 | Regan et al. | |
| 5,017,716 A | 5/1991 | Karanewsky et al. | |
| 5,021,453 A | 6/1991 | Joshua et al. | |
| 5,025,000 A | 6/1991 | Karanewsky | |
| 5,081,136 A | 1/1992 | Bertolini et al. | |
| 5,091,185 A | 2/1992 | Castillo et al. | |
| 5,091,378 A | 2/1992 | Karanewsky et al. | |
| 5,091,386 A | 2/1992 | Kesseler et al. | |
| 5,098,931 A | 3/1992 | Duggan et al. | |
| 5,102,911 A | 4/1992 | Lee et al. | |
| 5,112,857 A | 5/1992 | Vickers | |
| 5,116,870 A | 5/1992 | Smith et al. | |
| 5,130,306 A | 7/1992 | Duggan et al. | |
| 5,132,312 A | 7/1992 | Regan et al. | |
| 5,133,947 A | 7/1992 | Starnbaugh et al. | |
| 5,133,974 A | 7/1992 | Paradissis et al. | |
| 5,135,935 A | 8/1992 | Alberts et al. | |
| 5,166,171 A | 11/1992 | Jendralla et al. | |
| 5,182,298 A | 1/1993 | Helms et al. | |
| 5,196,440 A | 3/1993 | Bertolini et al. | |
| 5,202,327 A | 4/1993 | Robl | |
| 5,250,435 A | 10/1993 | Cover et al. | |
| 5,256,689 A | 10/1993 | Chiang | |
| 5,260,332 A | 11/1993 | Dufresne | |
| 5,262,435 A | 11/1993 | Joshua et al. | |
| 5,271,946 A | 12/1993 | Hettche | |
| 5,273,995 A | 12/1993 | Roth | |
| 5,276,021 A | 1/1994 | Karanewsky et al. | |
| 5,283,256 A | 2/1994 | Dufresne et al. | |
| 5,286,497 A | 2/1994 | Hendrickson et al. | |
| 5,286,895 A | 2/1994 | Harris et al. | |
| 5,302,604 A | 4/1994 | Byrne et al. | |
| 5,310,572 A | 5/1994 | Woodard et al. | |
| 5,317,031 A | 5/1994 | MacConnell et al. | |
| 5,356,896 A | 10/1994 | Kabadi et al. | |
| 5,369,125 A | 11/1994 | Berger et al. | |
| 5,378,475 A | 1/1995 | Smith et al. | |
| 5,385,932 A | 1/1995 | Vickers et al. | |
| 5,567,473 A * | 10/1996 | Lacz | D21H 17/36 |
| | | | 427/211 |
| 5,618,563 A | 4/1997 | Berde et al. | |
| 5,622,985 A | 4/1997 | Olukotun et al. | |
| 5,639,480 A | 6/1997 | Bodmer et al. | |
| 5,651,990 A | 7/1997 | Takada et al. | |
| 5,654,009 A | 8/1997 | Hata et al. | |
| 5,700,485 A | 12/1997 | Berde et al. | |
| 5,753,234 A | 5/1998 | Lee et al. | |
| 5,922,340 A | 7/1999 | Berde et al. | |
| 6,046,187 A | 4/2000 | Berde et al. | |
| 6,120,787 A | 9/2000 | Gustafsson | |
| 6,214,387 B1 | 4/2001 | Berde et al. | |
| 6,238,702 B1 | 5/2001 | Berde et al. | |
| 6,326,020 B1 | 12/2001 | Kohane et al. | |
| 6,426,339 B1 | 7/2002 | Berde et al. | |
| 6,544,646 B2 | 4/2003 | Vaghefi et al. | |
| 6,936,270 B2 | 8/2005 | Watson et al. | |
| 7,063,862 B2 | 6/2006 | Lin et al. | |
| 8,263,108 B2 | 9/2012 | Gibson et al. | |
| 8,765,725 B2 | 7/2014 | Cavanagh et al. | |
| 9,957,233 B1 | 5/2018 | Xi | |
| 2002/0114844 A1 | 8/2002 | Hanna et al. | |
| 2003/0152637 A1 | 8/2003 | Chasin et al. | |
| 2004/0191326 A1 | 9/2004 | Reo et al. | |
| 2004/0208833 A1 | 10/2004 | Hovey et al. | |
| 2005/0069591 A1 | 3/2005 | Bernstein et al. | |
| 2007/0003619 A1* | 1/2007 | Smith | A61K 9/146 |
| | | | 424/469 |
| 2007/0026527 A1 | 2/2007 | Delacourte et al. | |
| 2007/0218139 A1 | 9/2007 | Smith et al. | |
| 2008/0044476 A1 | 2/2008 | Lyons et al. | |
| 2008/0317805 A1 | 12/2008 | McKay et al. | |
| 2009/0082321 A1 | 3/2009 | Edelman et al. | |
| 2009/0264472 A1 | 10/2009 | Wohabrebbi et al. | |
| 2010/0196482 A1 | 8/2010 | Radovic-Moreno et al. | |
| 2011/0081420 A1 | 4/2011 | Barrows | |
| 2011/0238036 A1 | 9/2011 | Ashton | |
| 2012/0282298 A1 | 11/2012 | Bodick et al. | |
| 2013/0052264 A1 | 2/2013 | Chung et al. | |
| 2013/0122085 A1 | 5/2013 | Dalton et al. | |
| 2013/0316006 A1 | 11/2013 | Popov et al. | |
| 2013/0316009 A1 | 11/2013 | Popov | |
| 2013/0337073 A1 | 12/2013 | Oshima et al. | |
| 2015/0044271 A1 | 2/2015 | Slattery et al. | |

FOREIGN PATENT DOCUMENTS

| | | |
|---|---|---|
| EP | 2 113 013 A2 | 11/2009 |
| EP | 2 976 062 A1 | 1/2016 |
| GB | 2 241 889 A | 9/1991 |
| JP | 61-191609 U | 11/1986 |
| JP | 1-311024 A | 12/1989 |
| JP | 4-230210 A | 8/1992 |
| JP | 2006-521287 A | 9/2006 |
| JP | 2006-523613 A | 10/2006 |

(56) References Cited

FOREIGN PATENT DOCUMENTS

| | | | |
|---|---|---|---|
| JP | 2010-111592 A | 5/2010 | |
| JP | 2010-540447 A | 12/2010 | |
| JP | 2013-535489 A | 9/2013 | |
| RU | 2 262 355 C1 | 10/2005 | |
| WO | 98/13027 A1 | 4/1998 | |
| WO | 02/28371 A1 | 4/2002 | |
| WO | 2004/058222 A1 | 7/2004 | |
| WO | 2004/058223 A1 | 7/2004 | |
| WO | 2005/009604 A1 | 2/2005 | |
| WO | 2008/048770 A1 | 4/2008 | |
| WO | 2008/103123 A2 | 8/2008 | |
| WO | 2008/119033 A1 | 10/2008 | |
| WO | 2009/001697 A2 | 12/2008 | |
| WO | 2009/039262 A2 | 3/2009 | |
| WO | 2010/007446 A1 | 1/2010 | |
| WO | 2010/017265 A2 | 2/2010 | |
| WO | 2010/052896 A1 | 5/2010 | |
| WO | 2012/019009 A1 | 2/2012 | |
| WO | 2013/130619 A1 | 9/2013 | |
| WO | 2014/153541 A1 | 9/2014 | |
| WO | 2014/153541 A9 | 9/2014 | |
| WO | 2016/044799 A1 | 3/2016 | |

OTHER PUBLICATIONS

Office Action, dated Feb. 6, 2019, for Chilean Application No. 201801098, 19 pages. (w/ English Machine Translation).

Rabinow et al., "Intra-articular (IA) Ropivacaine Microparticle Suspensions Reduce Pain, Inflammation, Cytokine, and Substance P Levels Significantly More than Oral or IA Celecoxib in a Rat Model of Arthritis." *Inflammation* 38(1):40-60, 2015.

"Armstrong-Kropp Development Corporation's Applications", R.P. C., pp. 268-271, 1974.

"Whitehead Institute for Biomedical Research, Max-Planck-Gesellschaft Zur Forderung Der Wissenschaften Ev, Massachusetts Institute of Technology, and University of Massachusetts Medical Center", Intellectual Property Office of New Zealand—Patent Decisions, NZIPOPAT 21, 2009 (9 pages).

Arnsten et al. "Antiretroviral Therapy Adherence and Viral Suppression in HIV-Infected Drug Users: Comparison of Self-Report and Electronic Monitoring," *Clinical Infectious Diseases* 33:1417-1423, Oct. 15, 2001.

Bartlett et al., "Management of Anthrax," *Clinical Infectious Diseases* 35:851-858, Oct. 1, 2002.

Blauw et al., "Stroke, Statins, and Cholesterol: A Meta-Analysis of Randomized, Placebo-Controlled Double-Blind Trials With HMG-CoA Reductase Inhibitors," *Stroke* 28:946-950, 1997. (6 pages).

Burch et al., "Current Indications for ACE Inhibitors and HOPE for the Future," *The American Journal of Managed Care* 8:478-490, 2002, (17 pages).

Byron et al., "Effects of Heat Treatment on the Permeability of Polyvinyl Alcohol Films to a Hydrophilic Solute," *Journal of Pharmaceutical Sciences* 76(1):65-67, Jan. 1987.

Cadorniga et al., "In vitro evaluation of the dissolution rate of crystalline suspensions destined to intramuscular administration," *European Journal of Drug Metabolism and Pharmacokinetics* S3:379-384, 1991. (7 pages).

Cushenberry et al., "Potential Use of HMG-CoA Reductase Inhibitors for Osteoporosis," *The Annals of Phamacotherapy* 36:671-678, 2002. (9 pages).

David et al., "Depot fluphenazine decanoate and enanthate for schizophrenia (Review)," *The Cochrane Collaboration*, 2006, 137 pages.

Dechend et al., "Modulating Angiotensin II-Induced Inflammation by HMG Co-A Reductase Inhibition," *The American Journal of Hypertension* 14:55S-61S, 2001, (8 pages).

Endres et al., "Stroke protection by 3-hydroxy-3-methylglutaryl (HMG)-CoA reductase inhibitors mediated by endothelial nitric oxide synthase," *Proc. Natl. Acad. Sci. USA* 95:8880-8885, Jul. 1998.

Fassbender et al., "Effects of statins on human cerebral cholesterol metabolism and secretion of Alzheimer amyloid peptide," *Neurology* 59:1257-1258, 2002.

Fleckstein, "History of Calcium Antagonists," *Circ. Res.* 52 (suppl I):3-16, 1983. (15 pages).

Friedlander et al., "Postexposure Prophylaxis against Experimental Inhalation Anthrax," *The Journal of Infectious Diseases* 167:1239-1242, 1993.

Gennaro et al. (eds.), "Cardiovascular Drugs," *Remington: The Science and Practice of Pharmacy*, 19$^{th}$ ed., Williams & Wilkins, Baltimore, Maryland, USA, 1995, p. 963. (4 pages).

Gennaro et al. (eds.), "Solutions and Phase Equilibria," *Remington: The Science and Practice of Pharmacy*, 20$^{th}$ ed., Lippincott Williams & Wilkins, Baltimore, Maryland, USA, 2000, p. 209. (1 page).

Gennaro et al. (eds.), "Hormones and hormone antagonists," *Remington: The Science and Practice of Pharmacy*, 20$^{th}$ ed., Lippincott Williams & Wilkins, Baltimore, Maryland, USA, 2000, p. 1371. (3 pages).

Gharabawi et al., "Enhanced psychiatric and neurological outcomes in chronically psychotic patients treated for a year with long-acting, injectable risperidone," Annual Meeting American College of Neuropsychopharmacology, San Juan, PR, 2002, 1 page.

Houghton, "Angiotensin II Receptor Antagonists in Chronic Heart Failure," *Drugs* 62(10):1433-1440, 2002. (9 pages).

International Search Report, dated May 25, 2004, for International Application No. PCT/US03/41391. (2 pages).

International Search Report and Written Opinion, dated Dec. 22, 2015, for International Application No. PCT/US15/51072. (7 pages).

International Search Report and Written Opinion, dated Jun. 20, 2014, for International Application No. PCT/US2014/031502, 7 pages.

Jefferds et al., "Adherence to Antimicrobial Inhalational Anthrax Prophylaxix among Postal Workers, Washington, D.C., 2001," *Emerging Infectious Diseases* 8(10):113 8-1144, 2002.

Kaplan et al., "Pharmacokinetics of benzathine penicillin G: Serum levels during the 28 days after intramuscular injection of 1,200,000 units," *J. Pediatr* 115:146-150, 1989, (6 pages).

McCall et al., "Calcium entry blocking drugs: mechanisms of action, experimental studies and clinical uses," *Curr. Probl. Cardiol.* 10(8):1-80, 1985. (81 pages).

Mimran et al., "Angiotensin II receptor antagonists and hypertension," *Clin. and Exper. Hypertension* 21(5&6):847-858, 1999. (13 pages).

Möllmann et al., "Klinisch-pharmakologiche Aspekte unterschiedlicher Betamethason-Kristallsuspensionen, " *Fortschr. Med.* 95(14):972-978, 1977. (8 pages) (w/ English Summary—"Clinical-pharmacologic aspects of betamethasone dipropionate suspension and other betamethasone esters").

Office Action, dated Jan. 26, 2020, for Australian Application No. 2015317339, 3 pages.

Office Action, dated Aug. 1, 2020, for Brazilian Application No. BR112018008415-8, 7 pages. (w/ English Translation).

Office Action, dated Oct. 10, 2019, for Canadian Application No. 2,907,765, 3 pages.

Office Action, dated Mar. 22, 2021, for Chinese Application No. 201910668623.9, 9 pages. (w/ English Translation).

Office Action, dated Mar. 4, 2020, for European Application No. 15 841849.1, 5 pages.

Office Action, dated Jun. 29, 2020, for Indian Application No. 8857/DELNP/2015, 6 pages. (w/ English Translation).

Office Action, dated Oct. 22, 2020, for Indian Application No. 201817016199, 7 pages. (w/ English Translation).

Office Action (English Translation), dated Jun. 10, 2019, for Israel Application No. 241718, 4 pages.

O'Keefe et al., "Should an Angiotensin-Converting Enzyme Inhibitor Be Standard Therapy for Patients With Atherosclerotic Disease?," *Journal of the American College of Cardiology* 37(1):1-8, 2001. (9 pages).

Perico et al., "Angiotensin II receptor antagonists and treatment of hypertension and renal disease," *Curr. Opin. Nephrol. Hypertens.* 7:511-518, 1998. (9 pages).

Quraishi et al., "Depot haloperidol decanoate for schizophrenia (Review)," *The Cochrane Collaboration*, 2006, 37 pages.

(56) References Cited

OTHER PUBLICATIONS

Soulas et al., "Drug Release from Poly(dimethylsiloxane)-Based Matrices: Observed and Predicted Stabilization of the Release Rate by Three-Layer Devices," *Industrial & Engineering Chemistry Research 51*:7126-7136, 2012.

Subhaga et al., "Evaluation of an aliphatic polyurethane as a microsphere matrix for sustained theophylline delivery," *J. Microencapsulation 12*(6):617-625, 1995.

Supplementary European Search Report, dated Apr. 21, 2011, for European Application No. 03800247.3-1219 / 1585500, 3 pages.

Wong et al., "Nonpeptide Angiotensin II Receptor Antagonists. I. Pharmacological Characterization of 2-n-Butyl-4-chloro-1-(2-chlorobenzyl)imidazole-5-acetic acid, sodium salt (S-8307)," *The Journal of Pharmacology and Experimental Therapeutics 247*(1): 1-8, 1988, (8 pages).

\* cited by examiner

SUSTAINED RELEASE OF FORMULATIONS OF LOCAL ANESTHETICS

BACKGROUND

Technical Field

This disclosure relates to sustained release formulations of local anesthetics and methods of using the same for managing pain, in particular, postsurgical pain.

Description of the Related Art

Postsurgical pain is associated with various complications and can be protracted. The patients typically experience acute pain immediately after surgery and moderate to severe pain during the first 24 hours after discharge. Thereafter, although the pain decreases over time, it generally remains severe enough to interfere with daily activities and healing for several days after surgery.

Conventionally, postsurgical pain may be managed by opioid agents. Opioid agents produce analgesia by interacting with the opioid receptors in the central nervous system. However, opioids even at low doses can produce significant adverse events, such as respiratory depression, drowsiness and sedation.

Unlike the opioids, local anesthetics bind directly and reversibly to the intracellular portion of sodium channels located in the plasma membrane of nerve cells. Analgesia is produced as the decrease of the influx of sodium ions prevents the propagation of impulses along the nerve. The degree of nerve block is governed by the frequency with which the sodium channels are open and exposed to the drug. Typically, the smaller, pain-transmitting nerve fibers are more sensitive to local anesthetics than the larger nerve fibers that mediate touch and pressure.

In the immediate postsurgical period, temporary analgesia can be achieved by infiltration of local anesthetic into the surgical site at closure or injection of the local anesthetic into an appropriate peripheral nerve fascia or the surrounding area. However, local anesthetics have analgesic activity for much shorter duration than the duration of postsurgical pain. Thus, patients may experience breakthrough pain that necessitates the use of strong parenteral analgesics such as opioids.

Extending the duration of the local analgesic can be effective in managing postsurgical pain while decreasing or eliminating the need for opioids. For instance, a single-dose injection of a sustained release formulation of liposomal bupivacaine (EXPAREL®) reportedly achieves postsurgical pain control of up to 72 hours, about 10 times longer than the duration of action of conventional bupivacaine (7 hours or less). In particular, EXPAREL® provides sustained release of bupivacaine HCl from a multivesicular liposomal drug delivery system. The liposomal delivery system (Depo-Foam®) includes microscopic spherical particles composed of hundreds of nonconcentric aqueous chambers encapsulating the drug. Each chamber is separated from its neighboring chambers by a lipid bilayer membrane. Once administered, the liposomal structure progressively erodes, allowing the drug to be released over an extended period of time.

However, because membranes formed by lipid bi-layers are dynamic, they can be destabilized by a multitude of factors including pH, temperature, high drug loading and the like. Such destabilization can disrupt the desired release profiles by causing leakages or burst release of the encapsulated drug. Moreover, the liposomal delivery system is often constricted in the choice of drugs, because only water-soluble drugs are suitable to be encapsulated in the aqueous chambers.

Accordingly, there is a medical need to seek alternative delivery systems for achieving sustained release of local anesthetics.

BRIEF SUMMARY

Described herein are pharmaceutical formulations, injectable dosage forms and method of using the same for treating or managing pain, in particular, postsurgical pain. More specifically, the present disclosure provides injectable microparticles, each particle including a crystalline local anesthetic agent substantially encased in a polyvinyl alcohol (PVA) coating. The PVA coating remains substantially intact during the delivery period, while the local anesthetic agent releases by diffusing through the PVA coating. The release rate and duration are controlled by the PVA structure (including molecular weight, level of hydrolysis and crystallinity), the curing process of the PVA coating, and the thickness of the PVA coating, among other parameters.

Thus, one embodiment provides a pharmaceutical composition, comprising: a plurality of microparticles, each microparticle including: (1) one or more crystals of a local anesthetic agent; and (2) a polyvinyl alcohol (PVA) coating fully encapsulating the one or more crystals, wherein the PVA coating is at least 85% hydrolyzed and is about 1-30 wt % of the microparticle, and wherein the one or more crystals of the local anesthetic agent is about 70-99 wt % of the microparticle and each has at least one dimension in a range of 35-500 μm.

In a further embodiment, the local anesthetic agent is an aminoamide drug, in particular, ropivacaine.

In additional embodiments, the aminoamide drug or ropivacaine is in a free base form.

In further embodiments, the local anesthetic agent comprises more than one crystals bound by a therapeutically inactive agent.

In various embodiments, the PVA coating has a molecular weight (Mn) of 2-200 kDa and is at least 85% hydrolyzed. In other embodiments, the PVA coating has a molecular weight (Mn) of 140-190 kDa and is at least 99% hydrolyzed.

In a specific embodiment, the PVA coating is thermal cured and physically crosslinked at conditions such as curing at 100-135° C. for 2-8 hours.

In other embodiments, the PVA coating is chemically crosslinked in the presence of a crosslinking agent.

In more specific embodiments, the PVA coating comprises less than 5% by weight of the crosslinking agent.

Advantageously, the pharmaceutical composition described herein show a dissolution rate of the local anesthetic agent at least 5 times slower, or at least 7 times slower, or at least 10 times slower than the dissolution rate of an uncoated local anesthetic agent in the same dissolution medium.

A further embodiment provides a method for managing postsurgical pain at a wound site of a patient in need thereof, comprising either infusing to the wound site a therapeutically effective amount of the coated local anesthetic agent as described herein or injecting the coated local anesthetic agent into an appropriate peripheral nerve fascia or the surrounding area.

BRIEF DESCRIPTION OF THE SEVERAL VIEWS OF THE DRAWINGS

The following figures set forth embodiments in which like reference numerals denote like parts. Embodiments are illustrated by way of example and not by way of limitation in all of the accompanying figures wherein.

DETAILED DESCRIPTION

Figure 1A:
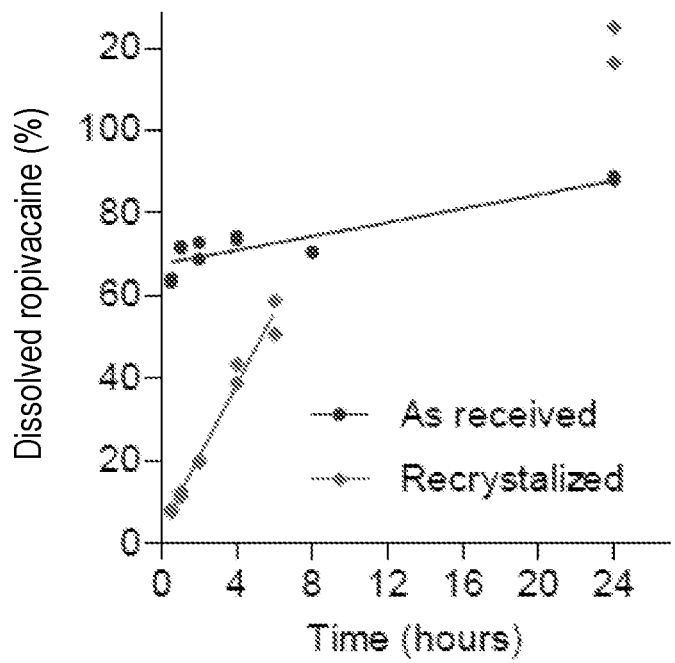
FIG. 1A shows the dissolution behaviors of commercial ropivacaine of finer crystals and the larger, recrystallized ropivacaine.

Described herein are pharmaceutical compositions, injectable dosage forms and method of using the same for treating or managing pain, in particular, postsurgical pain. More specifically, the present disclosure provides injectable microparticles, each particle including a crystalline local anesthetic agent substantially encased in a polyvinyl alcohol (PVA) coating. The PVA coating remains intact during the delivery period, while the local anesthetic agent releases by diffusing through the PVA coating. The release rate and duration are controlled by the curing process of the PVA coating and the thickness of the PVA coating, among other parameters.

As discussed in further detail herein, the injectable microparticles are characterized with high drug-loading, narrow size distribution and a sustained, steady release profile over a certain period within soft tissue (e.g., a wound site following surgery), or subcutaneously, or within a body compartment or a peripheral nerve fascia or the area surrounding a peripheral nerve fascia. In particular, for postsurgical pain management, the steady release may preferably take place over a period of 72 hours, or more preferably 96 hours.

The sustained and steady release delivery mechanism is based on dissolution. While not wishing to be bound by any specific mechanism of action, it has been found that when the crystalline drug coated with semi-permeable PVA membrane is injected into the tissue, fluid (water) from the tissue diffuses through the polymeric coating and partially dissolves the crystalline drug core. As a result, a saturated solution of the drug is formed inside the polymeric coating, which remains intact throughout the release period. Since there are essentially sink conditions in the fluid in which the microparticles are injected and reside, a concentration gradient is created which continuously drives the drug out of the microparticles and into the surrounding fluid. As long as there is some drug core remaining to maintain a saturated solution within the polymeric shell, a constant and steady release of the drug from the coated microparticles is obtained. The release mechanism is described in PCT/US2014/031502, which application is incorporated herein in its entirety.

Microparticles

The microparticles of the core/shell morphology described herein are constructed to exhibit a sustained release profile uniquely suited for highly localized, extended delivery of a local anesthetic agent, in particular, an aminoamide local anesthetic agent, which is in the form of crystals coated with polyvinyl alcohol (PVA).

More specifically, each drug-loaded microparticle includes (1) one or more crystals of a local anesthetic agent; and (2) a polyvinyl alcohol (PVA) coating fully encapsulating the one or more crystals, wherein the PVA coating is at least 85% hydrolyzed and is about 1-30 wt % of the microparticle, and wherein the one or more crystals of the local anesthetic agent is about 70-99 wt % of the microparticle and each has at least one dimension in a range of 35-500 μm.

Local Anesthetic Agent ("Drug")

Two classes of local anesthetic agents are suitable: aminoamide and aminoester local anesthetics.

Aminoamide local anesthetic agents include, without limitation ropivacaine, articaine, bupivacaine (levobupivacaine), dibucaine, etidocaine, lidocaine, mepivacaine, prilocaine, and trimecaine. In a particularly preferred embodiment the local anesthetic agent is ropivacaine.

Aminoester local anesthetic agents include, without limitation, benzocaine, chloroprocaine, cocaine, cyclomethycaine, dimethocaine (Larocaine), piperocaine, propoxycaine, procaine (Novocaine), proparacaine, and petracaine (Amethocaine).

It is found that larger crystals of a drug compound have lower rate of dissolution than the amorphous form or fine crystals of the same drug, resulting in a longer dissolution half-life and less initial burst. Larger crystals of the local anesthetic agents can be prepared by recrystallizing the amorphous powder or small fine crystals of the drug (which are the typical commercial forms).

FIG. 1A shows the dissolution behaviors of commercial ropivacaine as received (in fine powder form) and recrystallized ropivacaine. As shown, the rate of dissolution of the larger, recrystallized ropivacaine crystals is slowed by about 10 times as compared to commercial ropivacaine.

Figure 1B:
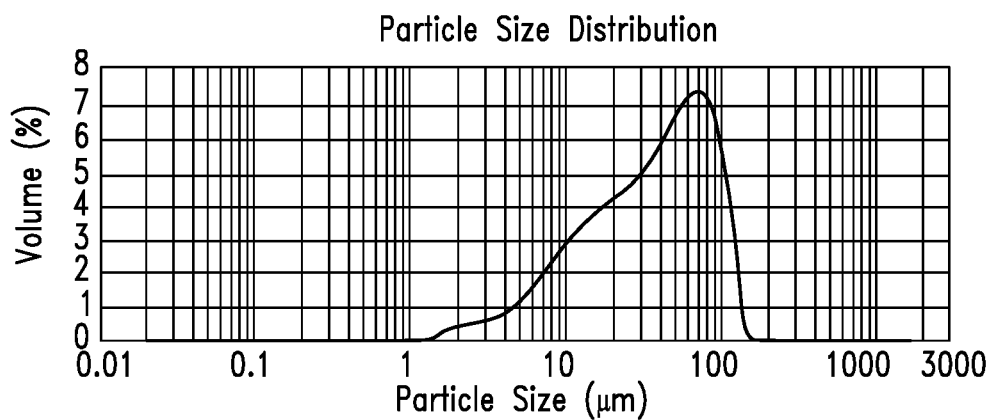
FIG. 1B shows particle size distribution of commercial ropivacaine fine powder.
Figure 1C:
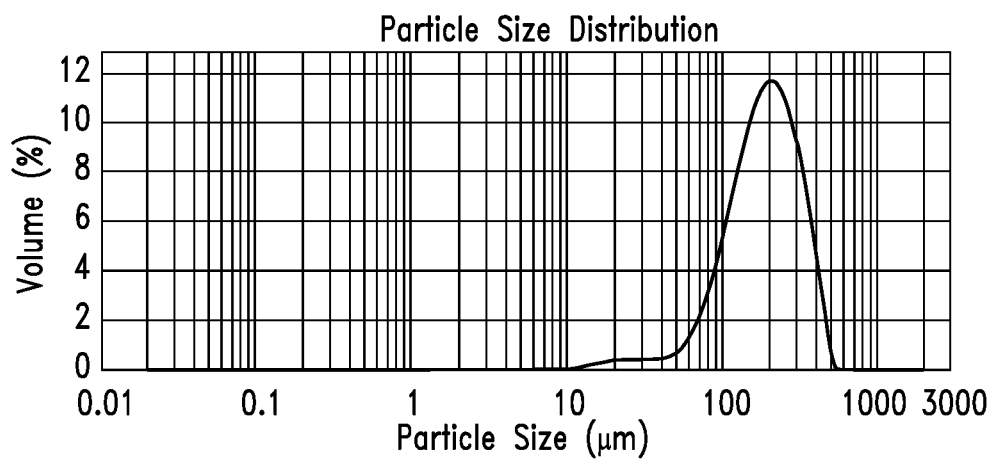
FIG. 1C shows particle size distribution of sieved ropivacaine recrystallized crystals.

Recrystallization produces large crystal dimensions, which make it possible to resize the drug crystals into substantially uniform dimensions. For example, fine crystals of ropivacaine (in the 100 μm or lower range) can be recrystallized (e.g., by slow-evaporation) to produce large crystals having dimensions in the millimeter range. The larger crystals can be resized (shortened) and sieved before coating. FIG. 1B shows the size distribution of commercial ropivacaine fine powders. As a comparison, FIG. 1C shows the size distribution of recrystallized ropivacaine crystals after resizing and sieving. As shown, not only are the recrystallized crystals are larger on average, they may also have narrower particle size distribution than the commercial fine powder.

Drug crystals that are recrystallized, resized and sieved can be better controlled to provide drug crystals of uniform size or shapes. In certain embodiments, the drug crystals have at least two dimensions that are substantially the same in sizes, providing an aspect ratio (i.e., length/diameter) of 1.

The local anesthetic agent thus comprises one or more recrystallized drug crystals having at least one dimension (e.g., the longest dimension) in the range of 35-500 μm, and more typically in the range of 75-300 μm, or more typically, in the range of 50-200 μm. In various embodiments, the crystals have at least one dimension in the range of 35-200 μm, or 75-200 μm, or 100-300 μm, or 100-200 μm, or 200-300 μm, or 200-400 μm. Larger crystals (e.g., ≥200 μm) may be coated individually; whereas one or more smaller crystals may be bonded into crystal aggregates or clusters before coating. When in aggregates, drug crystals may be bonded or glued together by a pharmaceutically inactive agent that serves as an adhesive.

In various embodiments, at least 90%, or at least 95% or at least 98%, or 100% of the entire weight of the crystalline drug is the local anesthetic agent. The drug-loading, i.e., the content of pure local anesthetic agent of the entire weight of the microparticle, is in turn about 70-99 wt %.

As used herein, the aminoamide local anesthetic agents are typically in the free base form, which have lower solubility in an aqueous medium than their salt form (e.g., HCl salt). The low solubility (e.g., less than 1 mg/ml) enables a rapid formation of a saturated solution within the PVA coating or shell. Table 1 shows the solubility of ropivacaine in various aqueous media that include PBS buffer (pH 7.4), sodium dodecyl sulfate (SDS), or bovine serum albumin (BSA).

TABLE 1

| Aqueous solutions | Solubility of ropivacaine (μg/mL) |
|---|---|
| PBS | 254 ± 13 |
| PBS + 0.05% SDS | 254 ± 14 |
| PBS + 0.1% SDS | 306 ± 18 |
| PBS + 0.2% SDS | 350 ± 12 |
| PBS + 68 mg/mL BSA | 792 ± 111 |

Because the PVA coating requires curing at elevated temperature (e.g., about 125° C.), the aminoamide local anesthetic agents should be heat-stable, at least at the curing temperatures. For example, ropivacaine (commercial or recrystallized) has a peak $T_m$ of about 148-149° C. and is shown to be stable below the melting temperature.

PVA Coating/Membrane

One or more crystals of the local anesthetic agent (e.g., recrystallized ropivacaine) are coated with polyvinyl alcohol (PVA). PVA is a water-soluble polymer that forms films easily at above certain molecular weight. The PVA coating substantially encases the crystals. Complete (100%) coverage is preferred but not required.

The PVA coating, also referred to as PVA membrane, is permeable to water and allows the formation of a saturated solution of the encapsulated local anesthetic agent. The dissolved local anesthetic agent then diffuses out of the PVA coating in a sustained and steady manner until the saturated solution can no longer be maintained (i.e., the local anesthetic agent is depleted). For postsurgical pain management, the period of sustained and steady release typically lasts 72 to 96 hours, or 72 to 120 hours (3-5 days) after administration or post-surgery.

The permeability of the PVA coating is determined by multiple factors, including the molecular weight, the degree of hydrolysis, the degree of crystallinity, the degree of crosslinking and the thickness of the coating. Without wishing to be bound to any theory, it is believed that as the PVA swells and progressively dissolves in a liquid medium, the permeability increases and drug diffusion occurs.

Suitable PVA has a molecular weight (Mn) in the range of 20-220 kDa, or more preferably 140-190 kDa. In various embodiments, the PVA has a molecular weight (Mn) in the range of 146-187 kDa. In other embodiments, the PVA has a molecular weight (Mn) in the range of 90-120 kDa.

Commercial PVA polymers are generally derived from polyvinyl acetate by hydrolysis (i.e., converting the acetate to hydroxy). Thus, PVA polymers are available at different degrees of hydrolysis.

The degree of hydrolysis influences the crystallinity of the PVA coating because the hydroxyl groups can form hydrogen bonds between PVA chains, thereby orienting them in an ordered fashion. Thus, a higher content of hydroxyl group (i.e., high degree of hydrolysis) typically is associated with a higher degree of crystallinity. Higher crystallinity renders the PVA membrane slower to dissolve, resulting in a slower diffusion of the encapsulated drug. Thus, as used herein, the PVA is at least 85% hydrolyzed, or at least 87% hydrolyzed, or preferably at least 98% or at least 99% hydrolyzed.

In order to achieve the desired permeability, the highly hydrolyzed PVA coating may be further thermally cured (physically crosslinked), chemically crosslinked or both.

The degree of the crystallinity of the PVA coating may be controlled by thermal curing at a certain temperature for a certain period of time, provided that the curing temperature is below the melting temperature of the crystalline local anesthetic agent. In various embodiments, suitable curing temperature may be in a range of 100-135° C. for 2-8 hours. In certain embodiments, the curing temperature is in the range of 120-135° C. for 4-8 hours. In a preferred embodiment, the PVA coating is cured at 125° C. for 6 hours. As a result of the thermal curing, the PVA chains may be physically crosslinked.

The degree of the permeability (dissolvability) of the PVA coating may also be controlled by chemically crosslinking between hydroxyl groups. The additional covalent bonding within the polymer structure impedes the dissociation of the polymer chains, thereby slowing down or prevents the dissolution of the PVA. Suitable crosslinkers include organic polyprotic acids, (i.e., acids having two or more carboxylic groups). In various embodiments, the crosslinker may be citric acid, tartaric acid, oxalic acid, succinic acid, gluconic acid and the like. In a preferred embodiment, the crosslinker is citric acid, which has three carboxylic acid groups. In various embodiments, crosslinking occurs by incorporating a crosslinker in the PVA solution prior to coating. Typically, the amount of crosslinker required depends on the level of hydrolysis of the PVA. For highly hydrolyzed PVA (87% or above) as used herein, less than 20%, or less than 12%, or less than 8% of the crosslinker is employed.

The degree of crystallinity may be measured by melting enthalpy. A higher degree of crystallinity is associated with a higher melting enthalpy and a higher glass transition temperature. Table 2 shows the effects of the degrees of hydrolysis, thermal curing and crosslinking on the crystallinity of PVA films (all PVA have Mn=146-186 kDa, data obtained from first heating cycle).

TABLE 2

| Degree of Hydrolysis | Curing | Citric acid (%) | Melting ($T_m$) | | | Degradation ($T_d$) | | |
|---|---|---|---|---|---|---|---|---|
| | | | Onset (° C.) | Peak (° C.) | Enthalpy (J/g) | Onset (° C.) | Peak (° C.) | Enthalpy (J/g) |
| 99% | As received | 0 | 209.69 | 222.05 | 55.2 | 243.93 | 261.40 | 501 |
| 99% | 125° C./6 h | 0 | 215.09 | 223.63 | 48.43 | 228.86 | 259.18 | 228.86 |
| 99% | | 4 | 209.82 | 216.68 | 50.77 | 272.64 | 303.53 | 542.6 |
| 99% | | 8 | 183.00 | 200.24 | 47.45 | 271.79 | 302.8 | 451.6 |
| 99% | | 12 | 179.00 | 199.48 | 24.55 | 299.34 | 312.12 | 227.4 |
| 87% | As received | 0 | 176.42 | 189.52 | 25.45 | Out of range | | |
| 87% | 125° C./6 h | 4 | 161.7 | 174.95 | 13.05 | 269.76 | 309.24 | 134.9 |
| 87% | | 8 | 144.81 | 158.81 | 22.46 | 279.09 | 317.77 | 139.6 |
| 87% | | 12 | 142.83 | 160.09 | 24.43 | 283.04 | 318.32 | 70.94 |

As shown, for highly hydrolyzed PVA (>99%), exposure to a crosslinking agent does not increase but could decrease crystallinity. It is believed that chemical crosslinking by a crosslinking agent such as citric acid may have disrupted the hydrogen bonding naturally present in the highly hydrolyzed PVA chains, resulting in a decreased degree of crystallinity.

The PVA coating should remain substantially intact during the sustained release period, though swelling (due to hydration) or minor/partial dissolution will likely take place concurrently with the drug release. PVA is water soluble due to the high content of hydroxyl groups. However, highly hydrolyzed PVA or crosslinked PVA have slower dissolution rates because of their highly ordered structure or the additional intrinsic covalent bonds, respectively. Thus, while 87%-hydrolyzed PVA coatings (following curing at 130° C. for 6.5 hours) can dissolve in water in one day, 87%-hydrolyzed PVA coatings exposed to 6% citric acid and cured under similar conditions remain intact for up to 158 days.

Compared to chemical crosslinking, physical-crosslinking by heating and curing can be advantageous. By forming physical crosslinking points (e.g., by creating additional hydrogen-bonding) without disrupting the naturally aligned hydrogen bonding in the highly hydrolyzed PVA chains, a physically-crosslinked PVA membrane can be optimized to provide the desired degrees of crosslinking and crystallinity.

Table 3 shows the DSC analysis of commercial PVA, PVA membrane and heat-treated PVA membrane (cured at 125° C. for 6 hrs, data obtained from second heating cycle). All PVA were 99% hydrolyzed with molecular weight of 146-186 kDa. As shown, the cured PVA membrane was physically crosslinked without little or no loss of crystallinity as evidenced by only slight changes in their melting points.

TABLE 3

| | Glass transition (Tg, ° C.) | Melting point on set (° C.) | Melting point peak (Tm, ° C.) | Melting enthalpy (Δ, J/g) |
|---|---|---|---|---|
| PVA | 76.80 | 218.09 | 225.68 | 51.26 |
| PVA membrane | 71.81 | 213.48 | 224.23 | 48.41 |
| Cured PVA membrane | 74.41 | 212.57 | 222.20 | 47.71 |

Methods of Forming Microparticles

Methods of forming polymeric coatings on particles are well known in the art. For example, standard techniques include solvent evaporation/extraction techniques, in-water drying techniques (see, e.g., U.S. Pat. No. 4,994,281), organic phase separation techniques (see, e.g., U.S. Pat. No. 5,639,480), spray-drying techniques (see, e.g., U.S. Pat. No. 5,651,990), air suspension techniques, and dip coating techniques.

Typically, a solution of PVA in water (1-15%) is prepared and spray-coated on the drug crystals, following recrystallization and sizing. One or more crystals may be substantially encased in a continuous membrane of PVA (though 100% coverage is not required). Where crosslinking is required (e.g., PVA less than 99% hydrolyzed), the crosslinker may be dissolved in the PVA solution prior to coating.

The coated particles are subject to thermal curing at a temperature of about 100-135° C. for 2-8 hours.

The PVA coating is typically about 1-20%, more typically, about 1-10% of the entire weight of the microparticle. The content of the PVA can be ascertained by NMR quantification by comparing certain selected peak areas (e.g., 3.7-4.0 ppm) with a standardized amount of PVA.

In various embodiments, the thickness of PVA coating can be in the range of 5-60 µm, or in the range of 10-30 µm. The thickness can be directly measured in SEM images. For instance, for coated ropivacaine particles, 10% of PVA (by weight) was shown to be less than 15 µm thick. The thickness of the PVA coating can be controlled by the concentration of the PVA solution for coating and the number of coatings. Thicker coatings result in slower diffusions.

Because the PVA coating is thin compared to the crystalline drug encapsulated, the microparticles formed substantially take the shapes and sizes of the encapsulated crystals. Thus, in various embodiments, the microparticles (when taking into consideration of the coating thickness) have at least one dimension (e.g., the longest) of 35-500 µm, or more typically, 75-300 µm. In certain embodiments, the coated particles have the same aspect ratio as the encapsulated drug crystals. Microparticles of these sizes are large enough for a large payload of the local anesthetic agent, yet small enough to be injected through a needle.

In Vitro Dissolution Characteristics

The in vivo sustained release profile is correlatable to the in vitro dissolution characteristics of the microparticles, which in turn are determined by, among others factors, the solubility of the local anesthetic agents, and the permeability of the PVA coating.

It is important to recognize that dissolution models are designed to give an approximation of the dissolution as compared to in vivo release. PCT/US2014/031502 demonstrates methods for quantifying in vitro dissolution characteristics in the context of a corticosteroid drug, which methods may also be extended to quantifying the dissolution characteristics of the microparticles described herein.

The dissolution characteristics can be measured as the percentage of dissolution over time, and graphed as a dissolution profile. A linear dissolution profile has a constant rate of dissolution as represented by the slope of the linear profile. Constant rate of dissolution is associated with zero-order release, i.e., the rate of release is irrespective of the amount of the drug encapsulated in the PVA coating. Besides providing quantitatively the dissolution amount as a function of time, the curvature of the profile qualitatively shows the extent of the initial burst. For example, a sharp rise in the curvature indicates a faster initial release (burst) when compared with a gentler rise.

Unless specified otherwise, the dissolution system used for measuring dissolution half-life of the microparticles is USP Type II (paddle). It is important to recognize that dissolution models are designed to give an approximation of the dissolution as compared to in vivo release. PCT/US2014/031502 demonstrates methods for quantifying in vitro dissolution characteristics in the context of a corticosteroid drug, which methods may also be extended to quantifying the dissolution characteristics of the microparticles described herein.

A typical dissolution model used herein is USP apparatus I. A typical small capacity apparatus has a 150 ml bath. Other parameters include for example, 25-200 rpm, 37° C. and 0.1% SDS/PBS.

Compared to the uncoated drug, the coated particles slow the dissolution rate of the encapsulated local anesthetic agent. The dissolution rates of the coated drug crystals are directly related to the permeability of the PVA coating, which is in turned determined by the thickness, molecular weight, degrees of crosslinking, degrees of crystallinity etc. of the PVA coatings. Thus, in certain embodiments, the dissolution characteristics of the coating drug crystals can be defined by the reduction of the dissolution rate of the coated drug crystals as compared to the dissolution rate of the same drug crystals but uncoated, as measured in the same dissolution medium. In various embodiments, the coated microparticles exhibit a dissolution rate of at least 10-fold reduction when compared to the dissolution rate of the uncoated drug crystals of the same dimensions in the same dissolution medium. In other embodiments, the reduction in dissolution rate may be 8 folds, 7 folds, 6 folds, 5 folds, 4 folds or 3 folds when compared to uncoated drug crystals.

The reduction in dissolution rate can be modulated by adjusting the degrees of crosslinking (physical or chemical), thickness, crystallinity of the PVA membrane. The dissolution rate is creatable to the in vivo release period. In various embodiments, the coated microparticles are capable of local, sustained release of 3-5 days.

Figure 2:
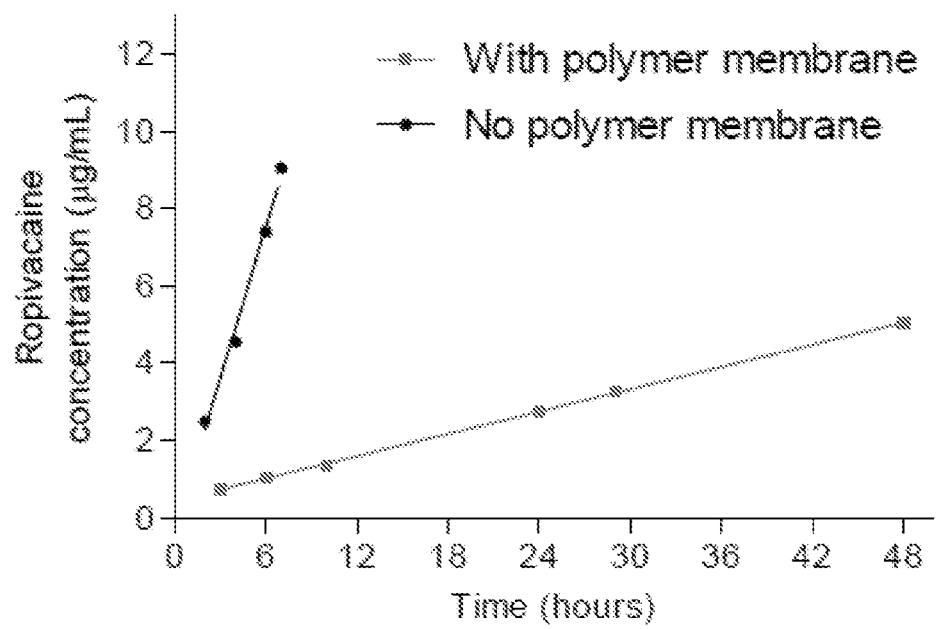
FIG. 2 shows the intrinsic dissolution of uncoated ropivacaine as compared to ropivacaine coated with PVA membrane.

FIG. 2 shows the intrinsic dissolution of ropivacaine, which is much more rapid than ropivacaine coated with PVA membrane (Mn=20-200 kDa, 87% hydrolyzed, crosslinked using 12% citric acid and cured at 125° C. for 6 hours).

Figure 6:
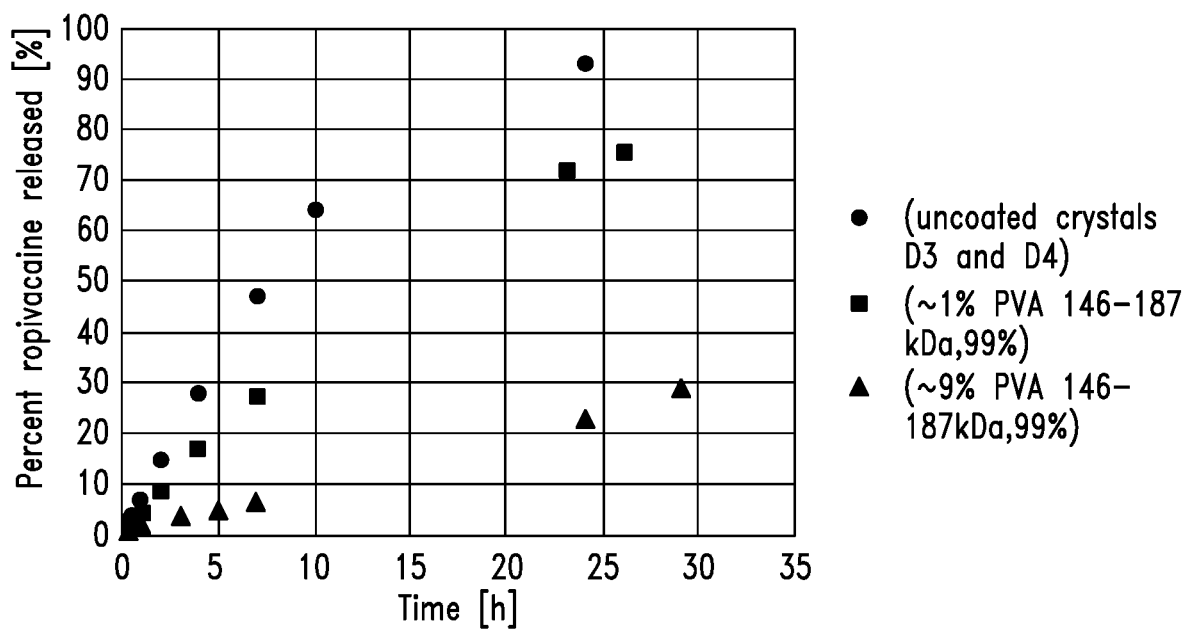
FIG. 6 shows the dissolution rate of ropivacaine from coated microparticles as impacted by the content (e.g., thickness) of the PVA coating (thermally cured).

FIG. 6 (see also Example 7) shows that, compared to the dissolution rate of uncoated ropivacaine crystals, coated ropivacaine crystals have much decreased rates of dissolution. More specifically, for 1% PVA (99% hydrolyzed and MW=146-187 kDa), the decrease in rate of dissolution is about 3.5 folds; whereas for particles with thicker coatings (9% PVA), the decrease is about 6.5 folds.

In vitro Diffusion Characteristics

When the coated microparticles are administered to a patient, water from the surrounding tissue permeates through the PVA membrane, forming a saturated solution of the encapsulated drug within the membrane. In a zero-order or pseudo-zero order release, the dissolved drug diffuses through the PVA membrane in a steady and sustained manner.

The diffusion behavior of the encapsulated drug in vivo can be predicted based on diffusion coefficient measured in a Franz cell diffusion system. In particular, diffusion coefficient (D) can be quantified according to Equation 1:

$$D = \frac{L \times J}{\Delta C} \qquad \text{Eq. (1)}$$

where:
D: Diffusion coefficient ($cm^2/s$)
L: membrane thickness (cm)
J: flux: ($\mu g \times cm^{-2} \times s^{-1}$)=slope ($\mu g/mL/h$)×volume (9.8 mL)÷(3600 s/h×A $cm^2$)
A: surface area of the Franz cell (0.650 $cm^2$)
$\Delta C$: concentration gradient of ropivacaine ($\mu g/mL$ or $\mu g/cm^3$)=339.98 $\mu g/mL$ (measured receptor fluid concentration)−0 $\mu g/mL$ (assumed donor concentration)

Table 4 summarizes diffusion through four polymers prepared as membranes using a range of curing conditions (temperature/time), cross-linking conditions (with varying amounts of citric acid). Table 3 also compares the values in terms of fold changes (decreases) in ropivacaine diffusion coefficient, relative to buffer with no membrane.

TABLE 4

| | | Cross-linking Parameters | | | Polymer Film Properties | | |
|---|---|---|---|---|---|---|---|
| % Hydrolysis | PVA Mn. (kDa) | % | Temp. (° C.) | Time (h) | Swelling (%) | D ($cm^2$/s) | Fold Decrease in D |
| 87 | 146-186 | 4 | 125 | 6 | 292 | 2.32E−07 | 21 |
| 87 | 146-186 | 12 | 125 | 6 | 122 | 2.90E−07 | 17 |
| 87 | 146-186 | 4 | 125 | 6 | 318 | 2.64E−07 | 19 |
| 87 | 146-186 | 12 | 125 | 6 | 162 | 3.85E−07 | 13 |
| 87 | 146-186 | 8 | 125 | 6 | 168 | 2.30E−07 | 22 |
| 87 | 146-186 | 8 | 125 | 6 | 167 | 2.93E−07 | 17 |
| 87 | 20-220 | 4 | 125 | 6 | 449 | 1.94E−07 | 26 |
| 87 | 20-220 | 4 | 125 | 6 | 509 | 2.23E−07 | 22 |
| 87 | 20-220 | 8 | 125 | 6 | 255 | 2.20E−07 | 23 |
| 87 | 20-220 | 8 | 125 | 6 | 230 | 3.01E−07 | 17 |
| 87 | 20-220 | 12 | 125 | 6 | 273 | 4.30E−07 | 12 |
| 87 | 20-220 | 12 | 125 | 6 | 285 | 5.43E−07 | 9 |
| 87 | 20-220 | 20 | 125 | 6 | 203 | 6.26E−07 | 8 |
| 87 | 20-220 | 20 | 125 | 6 | 233 | 3.64E−07 | 14 |

TABLE 4-continued

| | | Cross-linking Parameters | | | Polymer Film Properties | | |
|---|---|---|---|---|---|---|---|
| % Hydrolysis | PVA Mn. (kDa) | % | Temp. (° C.) | Time (h) | Swelling (%) | D (cm$^2$/s) | Fold Decrease in D |
| 87 | 20-220 | 30 | 125 | 6 | 148 | 4.88E-07 | 10 |
| 87 | 20-220 | 30 | 125 | 6 | 139 | 2.82E-07 | 18 |
| >99 | 90 | 8 | 125 | 6 | 183 | 1.68E-07 | 30 |
| >99 | 90 | 8 | 125 | 6 | 186 | 1.99E-07 | 25 |
| >99 | 90 | 12 | 125 | 6 | 235 | 3.59E-07 | 14 |
| >99 | 90 | 12 | 125 | 6 | 245 | 3.41E-07 | 15 |
| >99 | 90 | 20 | 125 | 6 | 137 | 2.38E-07 | 21 |
| >99 | 90 | 20 | 125 | 6 | 134 | 2.01E-07 | 25 |
| >99 | 146-186 | 0 | 125 | 6 | 59 | 9.09E-08 | 55 |
| >99 | 146-186 | 0 | 125 | 6 | 41 | 9.21E-08 | 54 |
| >99 | 146-186 | 0 | 129 | 3 | 81 | 1.47E-07 | 34 |
| >99 | 146-186 | 0 | 140 | 6 | 87 | 1.33E-07 | 37 |
| >99 | 146-186 | 0 | 140 | 6 | 56 | 1.19E-07 | 42 |
| >99 | 146-186 | 4 | 125 | 6 | 135 | 2.40E-07 | 21 |
| >99 | 146-186 | 4 | 125 | 6 | 129 | 2.15E-07 | 23 |
| >99 | 146-186 | 4 | 140 | 6 | 106 | 1.97E-07 | 25 |
| >99 | 146-186 | 4 | 140 | 6 | 113 | 1.44E-07 | 34 |
| >99 | 146-186 | 8 | 125 | 6 | 142 | 2.02E-07 | 25 |
| >99 | 146-186 | 8 | 125 | 6 | 178 | 1.91E-07 | 26 |
| >99 | 146-186 | 12 | 125 | 6 | 94 | 2.41E-07 | 21 |
| >99 | 146-186 | 12 | 125 | 6 | 105 | 2.18E-07 | 23 |

As shown in Table 4, PVA membranes of 146-186 kDa and >99% hydrolysis (after thermal curing and physical crosslinking) had the greatest impact on diffusion, causing a 50-times decrease in diffusion coefficient when compared to the diffusion of ropivacaine in PBS ($4.97 \times 10^{-6}$).

Pharmaceutical Compositions

The present disclosure provides a pharmaceutical composition comprising a plurality of drug-loaded microparticles, wherein each drug-loaded microparticle includes (1) one or more crystals of a local anesthetic agent; and (2) a polyvinyl alcohol (PVA) coating fully encapsulating the one or more crystals, wherein the PVA coating is at least 85% hydrolyzed and is about 1-30 wt % of the microparticle, and wherein the one or more crystals of the local anesthetic agent is about 70-99 wt % of the microparticle and each has at least one dimension in a range of 35-500 μm.

In a further embodiment, the pharmaceutical composition further comprises a pharmaceutically acceptable vehicle, in which the plurality of microparticles is suspended. It is preferred that the microparticles of therapeutic agent are mixed with the vehicle immediately prior to injection, so there is no time for the local anesthetic agent to dissolve into the vehicle and there is no or substantially no initial burst of drug prior to injection.

Unit Dosage Form

A unit dosage form is a pharmaceutical composition (including all the embodiments as described above) having a predetermined quantity of the drug-loaded microparticles which, after a single injection, provides sustained release of the local anesthetic agent for a specified period.

For postsurgical pain, the quantity of the microparticles in a unit dosage depends upon several factors including the surgical site and the volume required to cover or fill the area. In various embodiments, the unit dosage form comprises 100-3000 mg of local anesthetic agent. In other embodiments, the unit dosage form comprises 500-2000 mg of therapeutic agent. For example, in a soft tissue surgery (hemorrhoidectomy), about 1600 mg of the local anesthetic agent constituted in a volume of 3 ml could be administered. In an orthopedic model (bunionectomy), a dose of about 600 mg in 8 ml could be administered. Other factors include the body weight and the age of the patient, the severity of pain, or the risk of potential side effects considering the general health status of the person to be treated.

Advantageously, because the drug-loaded microparticles described herein are capable of steady release with little initial burst, the initial loading of the drug in the unit dosage form can be rationally designed according to the desired sustained release period. In various embodiments, the sustained release period is 72 hours or 96 hours.

In various embodiments, the unit dosage form may be a syringe pre-filled with the appropriate amount of the microparticles. Immediately prior to infusion, a vehicle may be drawn into the syringe to reconstitute the microparticles. Advantageously, because of the lack of initial burst, any dissolution of the drug into the vehicle during normal handling time in preparation for an injection is insignificant. In contrast, many known drug-loaded sustained release formulations are capable of saturating the vehicle during handling time due to an initial burst.

Methods of Using and Routes of Administration

The pharmaceutical compositions and dosage forms described herein can be used for subcutaneous, peripheral nerve blockade, intrathecal, epidural, or intraperitoneal administrations.

The pharmaceutical compositions are particularly suited to be injected into a body compartment for highly localized, sustained release of local anesthetic agent. The body compartment typically contains soft tissue and/or fluid within an enclosure or semi-enclosure. The injection is directed to the soft tissue or the fluid, into which the drug-loaded microparticles are released. When needed, the injection can be guided by an imaging system such as an ultrasonic or X-ray device.

One embodiment provides a method for reducing or managing pain, e.g., due to surgical pain, by administering an injectable dosage form to a body wound site before closure. Advantageously, the release is highly localized within the local tissue or fluid medium of the wound site to ensure a long-acting local therapeutic level, while maintaining a low or undetectable systemic level of the drug.

In a further embodiment, prior to infusion, the method includes administering a fast-acting local anesthetic agent such as lidocaine or uncoated ropivacaine, may be administered to provide immediate pain relief.

Another embodiment provides a method for reducing or managing pain, e.g., due to surgical pain, by administering an injectable dosage form to a peripheral nerve fascia or the area surrounding a peripheral nerve fascia. Advantageously, the release is highly localized to the particular nerve to ensure a long-acting local therapeutic level, while maintaining a low or undetectable systemic level of the drug.

EXAMPLES

Example 1

Recrystallization of Ropivacaine

Commercial ropivacaine contained a significant portion of fine particles (~50%). The presence of very small particles is believed responsible for initially rapid dissolution of ropivacaine particles (FIG. 1A). To overcome this problem, commercial ropivacaine was recrystallized and resized using standard sieves.

Ropivacaine was recrystallized by cooling a saturated hot solution of ropivacaine, prepared in methanol, 2-propanol or a mixture of both to room temperature (natural cooling). Crystals were separated by vacuum filtration. Large crystals of up to 2000 µm were obtained.

A specific recrystallization process involved slow evaporation of a sub-saturated methanol solution of ropivacaine. More specifically, 20 g of ropivacaine was dissolved in 165 ml methanol at room temperature under stirring; and the solution was let to evaporate slowly over 5-7 days. The process produced large ropivacaine crystals of several millimeters long.

The large crystals were resized by wet milling using a mortar and pestle in a suitable solution such as 50/50 methanol/water, and passed through standard sieved by squirting a suitable solution such as 50:50 methanol/water. Sieves with a range of mesh size were used: 106, 212, 250 and 300 µm. FIG. 1C shows the particle size distribution of ropivacaine crystals formed after recrystallization (slow evaporation), wet milling and wet sieving.

Table 5 summarizes the particle sizes of ropivacaine crystals obtained from different recrystallization processes (including different solvent systems). Commercial ropivacaine crystals are also presented as comparison.

TABLE 5

| Crystallization Solvent | Sieving Fraction | Median size (µm) $d_{(50\%)}$ |
|---|---|---|
| Commercial | Not sieved | 41.9 |
| Methanol | 250-300 µm | 243.1 |
| Methanol (slow evaporation) | 106-300 µm | 193.0 |
| Methanol/2-propanol | 106-212 | 240.1 |
| Commercial (sieved) | >212 µm | 369.0 |

The larger, recrystallized particles may have smaller/finer crystals attached to the surface. To remove these finer crystals, the recrystallized particles were suspended in a PVA solution, and washed with water. Alternatively, the fine crystals may be removed by washing with a mixture of methanol and water during the wet sieving process.

Example 2

Quantification of Ropivacaine in Solution

A Waters UPLC system equipped with a PDA detector was used for isolating and quantifying ropivacaine in buffer solutions. Separation was performed by reverse phase chromatography using a Waters BEH C18 column of 2.1×50 mm dimension and 1.7 µm particle size. An aqueous mobile phase of 10 mM ammonium acetate adjusted to pH 10 combined with acetonitrile were used in a gradient fashion to retain and elute Ropivacaine. A detection wavelength of 206 nm was used for optimum response.

The method was evaluated over a range of 0.5-50 µg/mL ropivacaine in 50/50 water acetonitrile (ACN) and in 0.1% SDS in PBS, using 10 µL injection volumes (full loop). The lowest limit of quantitation was 0.5 µg/mL in both solvent systems with an associated precision of within 2% RSD and an average accuracy (percent deviation from theoretical value) of 1%. The calibration curve displayed some loss of linearity (saturation) at the upper limit (50 µg/mL) but a linear fit with 1/x results in excellent accuracy and precision in the low range. Current experiments are performed over a range of 0.5-25 µg/mL in order to avoid saturation effects.

Example 3

Dissolution of Ropivacaine

Prior to assessing intrinsic dissolution of ropivacaine, the kinetics of dissolution of crystals in suspension was assessed using a USP I apparatus with either large (1 L capacity, filled to 500 mL) or small (150 mL) dissolution baths. The stir speed was 50 rpm in the large vessel method and 100 rpm in the small vessel method and temperature was 37° C. The media was PBS with 0.1% SDS. The commercial ropivacaine was dissolved rapidly with greater than 60% of the material dissolved within 30 minutes. A 17 mg sample dissolving in the large vessel reached a plateau within 4 hours, although only approximately 80% of the ropivacaine added to the experiment was accounted for.

In contrast, ropivacaine recrystallized from methanol did not exhibit the same burst phase, instead showing gradual dissolution over the first 6 hours, accounting for 60% of the material. Approximately 100-120% of the compound was accounted for in this assay. Regression analysis demonstrates that dissolution in the small vessel apparatus was essentially linear after a "burst phase" of dissolution within the first 30 minutes. The Y-intercept values of the regression is representative of the magnitude of the "burst", which was 25× higher for the commercial sample compared to the recrystallized sample. See also FIG. 1A.

Example 4

Diffusion of Ropivacaine Crystal Through PVA Membranes

The diffusion of ropivacaine through PVA membranes was measured using a Franz diffusion cell system. The system includes a top donor chamber containing a donor fluid, which is sealed with parafilm during the experiment; and a bottom receptor chamber containing a receptor fluid (9.8 mL of PBS pH 7.3). The donor fluid was prepared in a single batch for use in all diffusion experiments, and consisted of PBS pH 7.3. It was prepared by stirring excess solid ropivacaine in the media for 3 days, and filtering to remove the solids with a 0.22 µm filter. The assayed content was 339.98 µg/m L.

The rate of appearance of ropivacaine in the Franz cell receptor fluid (the slope of the concentration versus time plot of the data multiplied by the receptor cell volume, 9.8 mL), and the measured membrane thickness (after hydration), were used to calculate the ropivacaine diffusion coefficient through the membrane, using the formula for Fick's law (Equation 1).

Figure 3:
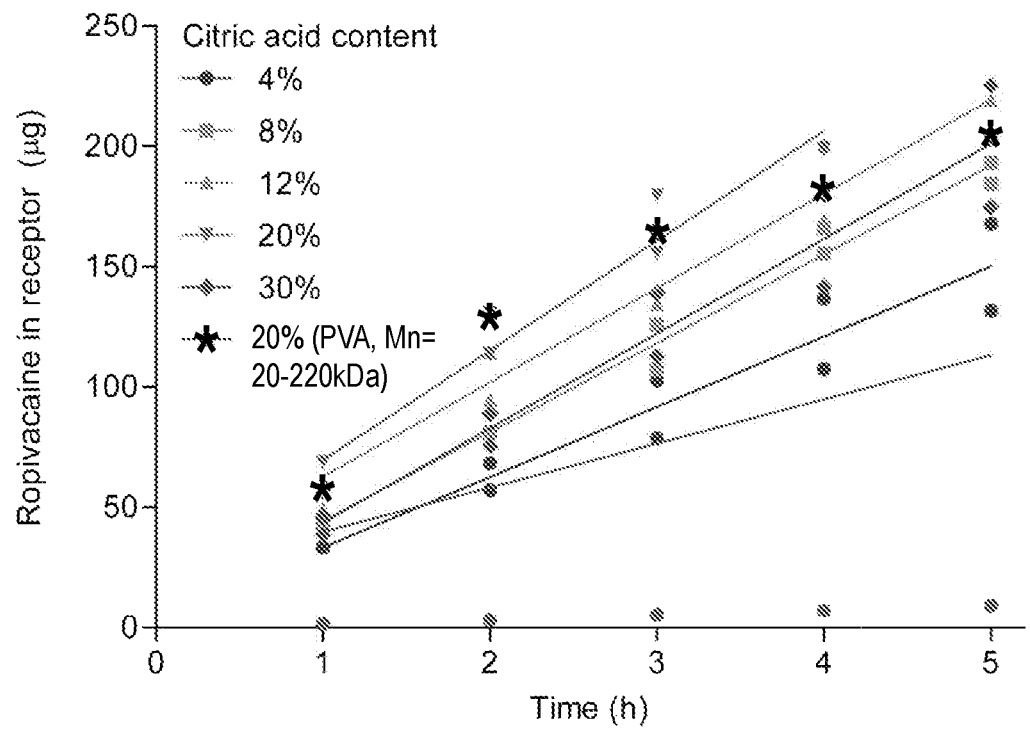
FIG. 3 shows the diffusion rate for the first 5 hours for PVA membranes (146-186 kDa, 87% hydrolyzed) at various degrees of crosslinking.
Figure 4:
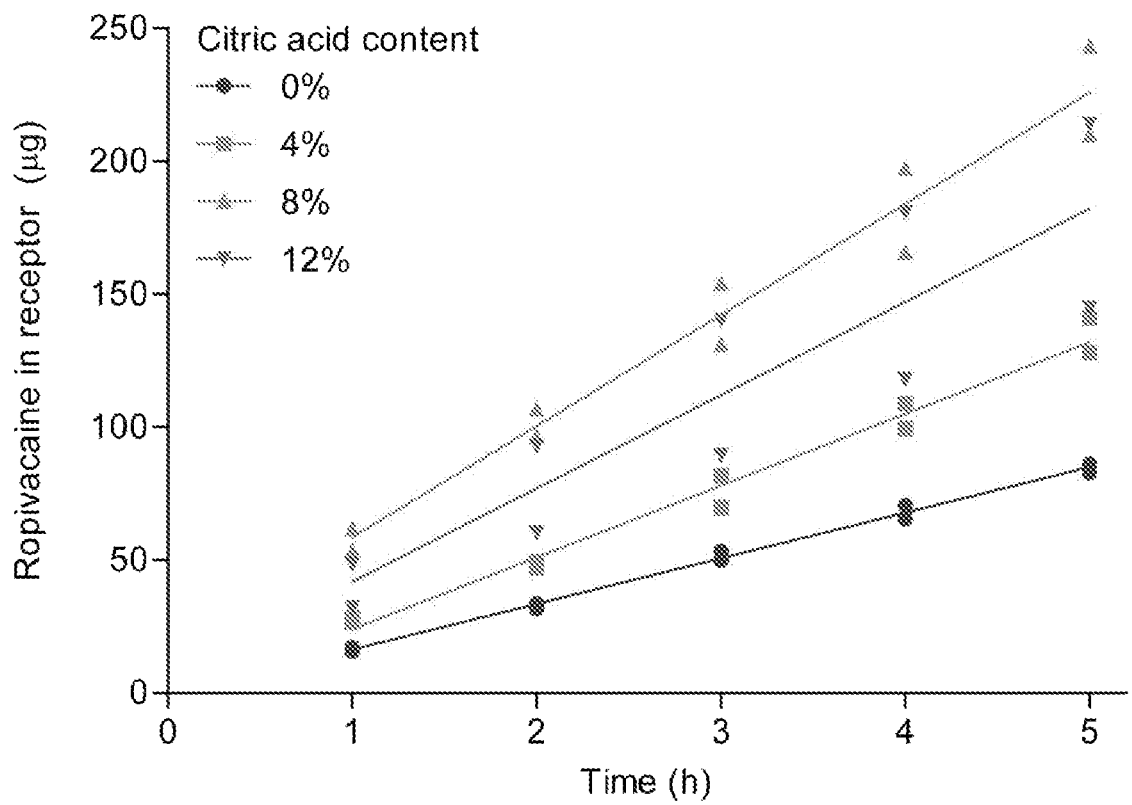
FIG. 4 shows the diffusion rate for the first 5 hours for PVA membranes (146-186 kDa, 99% hydrolyzed) at various degrees of crosslinking.
Figure 5:
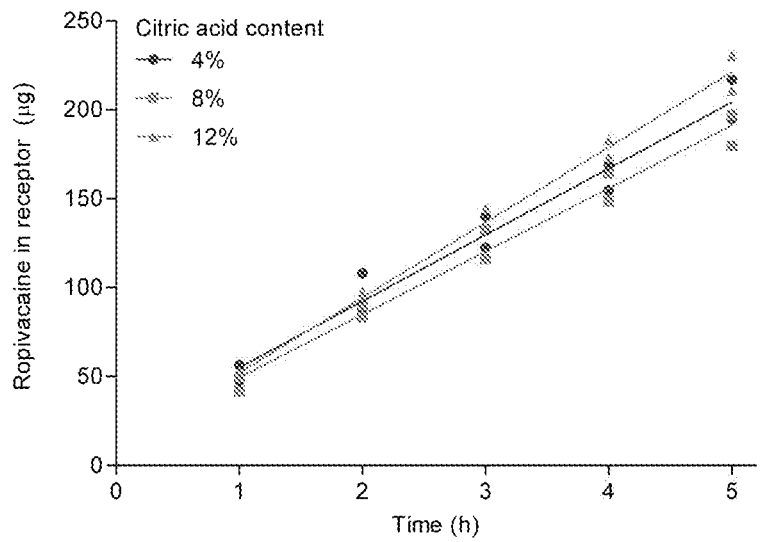
FIG. 5 shows the diffusion rate for the first 5 hours for PVA membranes (20-220 kDa, 87% hydrolyzed) at various degrees of crosslinking.

The concentration of ropivacaine in the receptor (bottom) chamber was measured at different time points, and the diffusion coefficient was determined from Fick's first law of diffusion. Measured concentrations were converted to total drug transport (μg) by multiplying by the receptor fluid volume (9.8 mL for all experiments). FIGS. 3-5 show the diffusion rate for the first 5 hours for three PVA membranes at various degrees of crosslinking induced by various amounts of citric acid. All three PVA membranes exhibited linear rate of ropivacaine diffusion. In particular, FIG. 3 shows the diffusion rate for PVA (146-186 kDa, 87% hydrolyzed). FIG. 4 shows the diffusion rate for PVA (146-186 kDa, 99% hydrolyzed). FIG. 5 shows the diffusion rate for PVA (20-220 kDa, 87% hydrolyzed).

Example 5

Coating Ropivacaine Crystals

Crystals were coated by spray coating by first preparing a PVA solution, including if needed, a crosslinking agent. One or more crystals of the recrystallized ropivacaine were coated and visualized by SEM to determine the completeness of the coating. Larger crystals may be individually coated; however, more than one crystals could be encapsulated within the coating.

Figure 7:
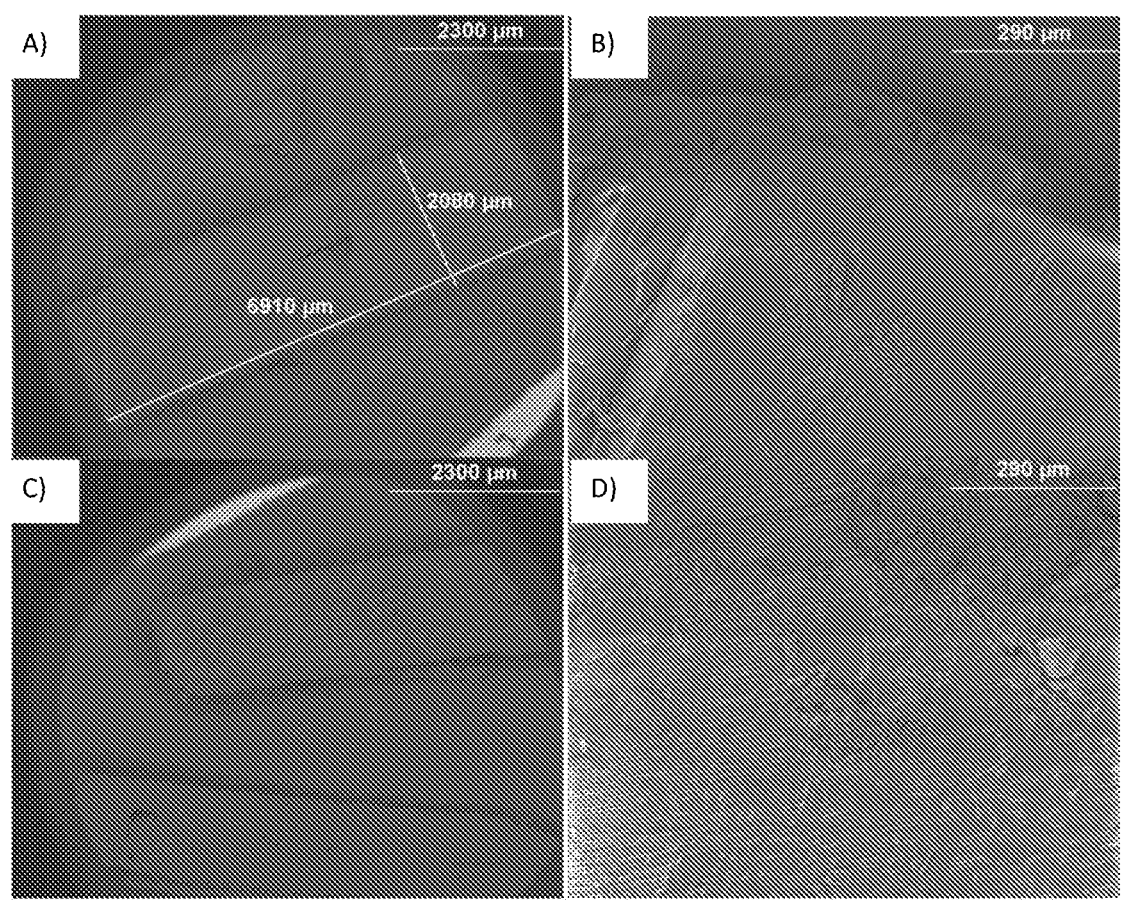
FIG. 7 shows the SEM images of uncoated particles (A and B) and coated particles (C and D) by PVA.

FIG. 7 shows the SEM images of uncoated particles (A and B) and coated particles (C and D) by PVA (90 kDa, 99% hydrolysis) containing 8% citric acid, following heat treatment 125° C. for 6 hours. As shown, the coating appeared complete (qualitatively), with coated crystals having a continuous, striated appearance. The coating also appeared to be thin and conformal. There was no distortion of the shape of the underlying crystal (e.g., edges and discontinuities appeared well defined despite coating).

Example 6

NMR Analysis for Determining PVA Content

NMR analysis was used to determine the amounts of the PVA in microparticles by calibrating with samples of known quantity of PVA. A standard curve to quantify the amount of PVA in a sample containing PVA and ropivacaine was generated by identifying non-overlapping regions of the proton NMR spectra of the two components (the peak between 3.7-4.0 ppm was selected), and integration of the selected peak in solutions containing a standardized amount of PVA. The concentration dependent peak area provided a linear relationship over the range of 4-20% w/v PVA concentration in solution (R2=0.999).

Example 7

Microparticles Dissolution Analysis

Dissolution of ropivacaine microparticles was slowed after PVA coating, compared with uncoated crystals, and the effect was proportional to the amount of PVA coating.

FIG. 6 shows the dissolution of ropivacaine as impacted by the content (e.g., thickness) of the PVA coating. As shown, for the highly hydrolyzed PVA coating (Mn=146-187 kDa, 99% hydrolysis), a higher content of PVA (9%) markedly slows down the ropivacaine diffusion as compared to the particles of lower content PVA or uncoated particles. In particular, the 9% PVA coated particles showed a dissolution rate (%/hr) that was about 7 folds slower than the uncoated particles.

Figure 8A:
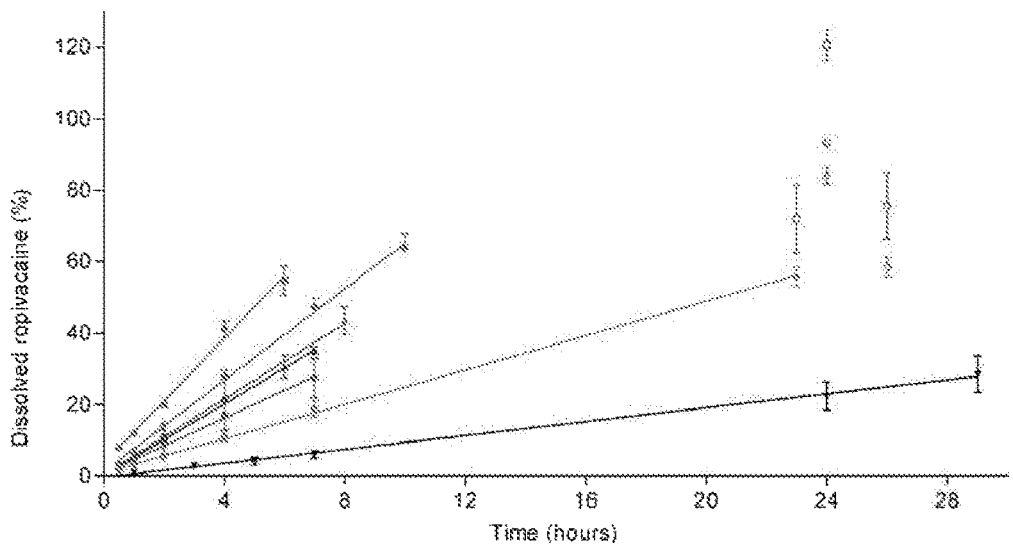
FIGS. 8A and 8B show the slowed dissolution of coated ropivacaine crystals was proportional to the amount of PVA coating.

As shown in FIG. 8A, all microparticles exhibited a linear rate of dissolution for at least 6 hours. Microparticles coated with 9% PVA and without crosslinking had a constant rate of dissolution over 29 hours. A 10 folds reduction in rate of dissolution (slopes of the linear dissolution profile, see also FIG. 8B) was observed comparing the uncoated crystals and 1% coated microparticles.

Figure 8B:
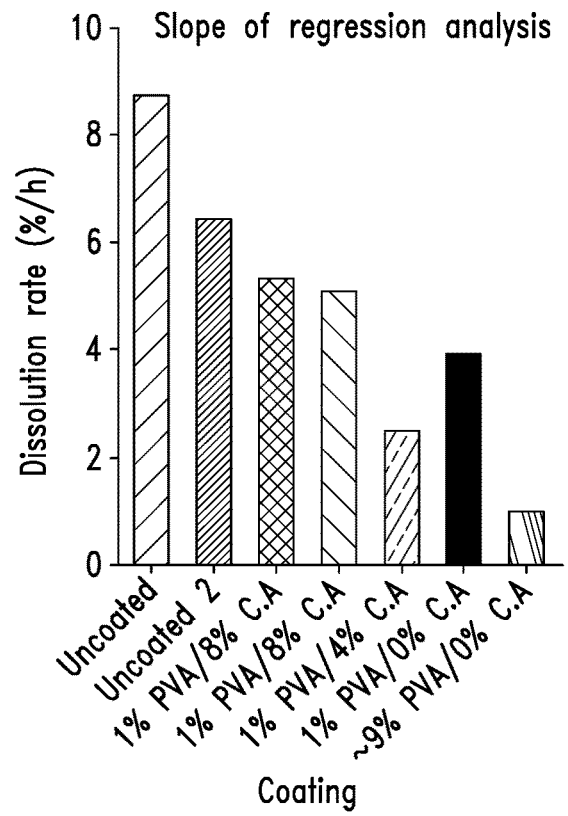

Also shown in FIG. 8B, for highly hydrolyzed PVA (99%) at 1% content, mild chemical crosslinking (4% citric acid) appeared to cause a decrease in dissolution rate when compared to thermally cured coated particles (0% citric acid), suggesting that the additional covalent bonds formed by the crosslinking agents reduced the dissociation of polymer chains and membrane permeability. However, an increase in chemical crosslinking (8% citric acid) caused an increase in dissolution rate, suggesting that enhanced chemical crosslinking might have lowered the crystallinity of the PVA membrane, which in turn increased the membrane permeability. FIG. 8B shows that thermally curing or physical crosslinking (0% citric acid) at 9% PVA (thicker membrane) had the lowest the dissolution rate.

Example 8

Physical Crosslinking PVA Membrane

Thermally cured PVA membranes were physically crosslinked without being chemically altered. PVA membrane (99% hydrolyzed, MW=146-186 kDa) were cured at 125° C. for 6 hrs.

Figure 9:
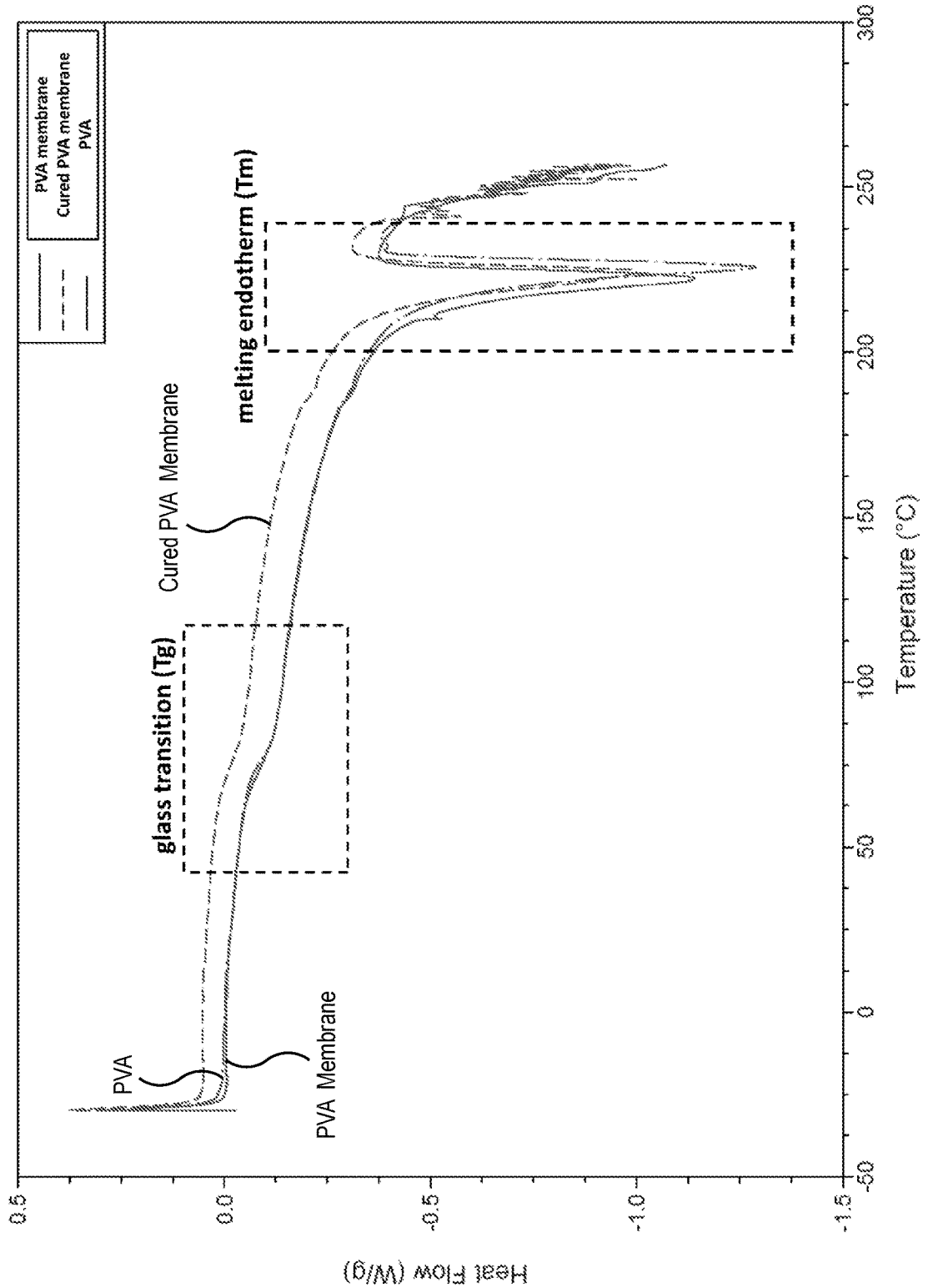
FIG. 9 shows the DSC curves of commercial PVA, PVA membrane and thermally cured PVA membrane.

FIG. 9 shows the DSC curves (obtained from the second heating cycle) of PVA membrane, cured PVA membrane and commercial PVA. As shown (see also Table 3), the thermally cured, physically crosslinked PVA membrane exhibited similar glass transition temperature, melting point as uncured PVA membrane or commercial PVA.

Figure 10:
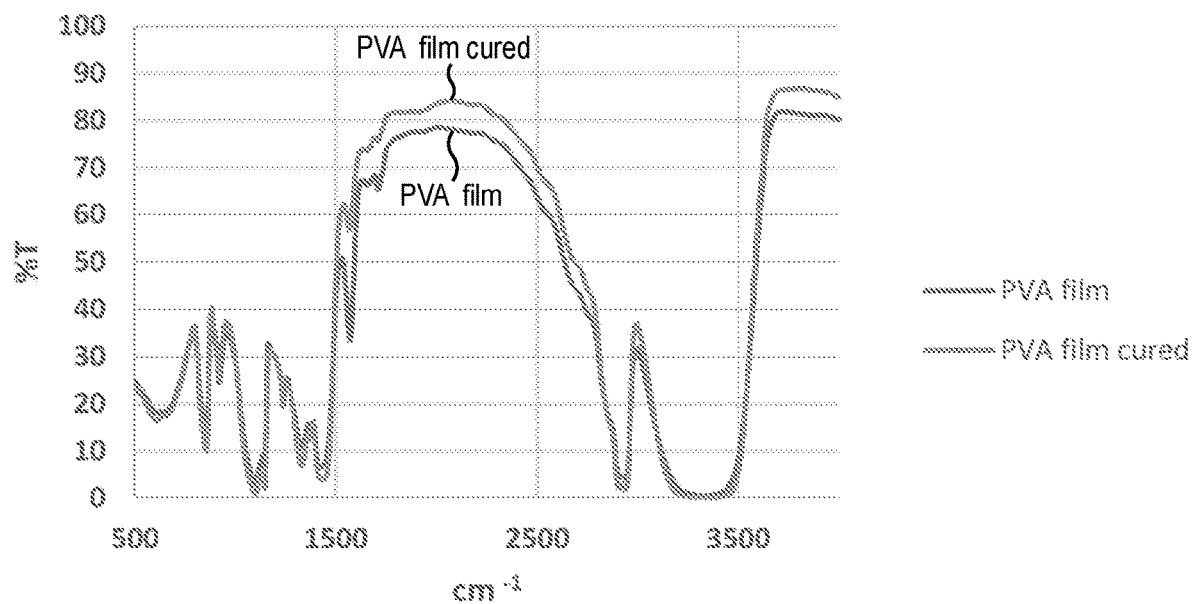
FIG. 10 shows the FTIR spectra of PVA membrane (uncured) and thermally cured PVA membrane.

FIG. 10 shows the FTIR spectra of PVA and cured PVA membrane. No formation of new functional groups was observed in FTIR analysis.

The absence of any newly formed chemical bonds in the cured PVA membrane was also confirmed by NMW spectra.

All of the above U.S. patents, U.S. patent application publications, U.S. patent applications, foreign patents, foreign patent applications and non-patent publications referred to in this specification and/or listed in the Application Data Sheet, including U.S. patent application Ser. No. 62/247,159, filed Oct. 27, 2015 are incorporated herein by reference, in their entirety.

We claim:

1. A pharmaceutical composition, comprising:
   a plurality of microparticles, each microparticle including:
   (1) one or more crystals of a local anesthetic agent; and
   (2) a polyvinyl alcohol (PVA) coating fully encapsulating the one or more crystals, wherein the PVA coating is at least 99% hydrolyzed and is about 1-30 wt % of the microparticle, and wherein the one or more crystals of the local anesthetic agent is about 70-99 wt % of the microparticle and each microparticle has at least one dimension in a range of 35-500 μm, and wherein the local anesthetic agent is an aminoamide drug.

2. The pharmaceutical composition of claim 1 wherein the PVA coating is crosslinked.

3. The pharmaceutical composition of claim 1 wherein the PVA coating is thermally cured and physically crosslinked.

4. The pharmaceutical composition of claim 3 wherein the thermal curing takes place at 100-135° C. for 2-8 hours.

5. The pharmaceutical composition of claim 1 wherein the PVA coating is chemically crosslinked in the presence of a crosslinking agent.

6. The pharmaceutical composition of claim 5 wherein the PVA coating comprises less than 5% by weight of the crosslinking agent.

7. The pharmaceutical composition of claim 5 wherein the crosslinking agent is citric acid.

8. The pharmaceutical composition of claim 1 wherein the PVA coating has a molecular weight of 2-200 kDa.

9. The pharmaceutical composition of claim 8 wherein the PVA coating has a molecular weight of 140-190 kDa.

10. The pharmaceutical composition of claim 1 wherein the local anesthetic agent has a dissolution rate of at least 5 times slower than that of the local anesthetic agent, when uncoated, in a same dissolution medium.

11. The pharmaceutical composition of claim 1 wherein the local anesthetic agent has a dissolution rate of at least 7 times slower than that of the local anesthetic agent, when uncoated, in a same dissolution medium.

12. The pharmaceutical composition of claim 1 wherein the local anesthetic agent has a dissolution rate of at least 10 times slower than that of the local anesthetic agent, when uncoated, in a same dissolution medium.

13. The pharmaceutical composition of claim 1 wherein the local anesthetic agent comprises more than one crystals bound by a therapeutically inactive agent.

14. The pharmaceutical composition of claim 1 wherein the local anesthetic agent is ropivacaine.

15. A method of managing postsurgical pain at a wound site of a patient in need thereof, comprising infusing to the wound site a therapeutically effective amount of the pharmaceutical composition of claim 1.

16. A method of managing postsurgical pain at a wound site of a patient in need thereof, comprising administering an injectable dosage form to a peripheral nerve fascia or the area surrounding a peripheral nerve fascia a therapeutically effective amount of the pharmaceutical composition of claim 1.

17. The method of claim 15 wherein the local anesthetic agent is sustained released for 3-5 days post-surgery.

* * * * *